United States Patent [19]

Konz et al.

[11] Patent Number: 4,673,682

[45] Date of Patent: Jun. 16, 1987

[54] ISOQUINOLINE DERIVATIVES, PHARMACEUTICAL FORMULATIONS BASED ON THESE COMPOUNDS AND THE USE THEREOF

[75] Inventors: Elmar Konz, Kelkheim; Joachim Kaiser, Frankfurt am Main, both of Fed. Rep. of Germany

[73] Assignee: Hoechst Aktiengesellschaft, Frankfurt, Fed. Rep. of Germany

[21] Appl. No.: 530,000

[22] Filed: Sep. 7, 1983

[30] Foreign Application Priority Data

Sep. 9, 1982 [DE] Fed. Rep. of Germany ....... 3233424

[51] Int. Cl.$^4$ ..................... A61K 31/47; C07D 217/16
[52] U.S. Cl. .................... 514/307; 514/222; 514/234; 514/238; 514/253; 544/62; 544/128; 544/363; 546/144
[58] Field of Search ................ 546/144; 514/307, 222, 514/234, 238, 253; 544/62, 128, 363

[56] References Cited

U.S. PATENT DOCUMENTS 4,260,611 4/1981 Bartmann et al. .................. 546/139

FOREIGN PATENT DOCUMENTS 875797 10/1979 Belgium .
7010358 1/1971 Netherlands .

OTHER PUBLICATIONS

Lucas, *Organic Chemistry*, Sec. Ed., 1953, American Book Co., pp. 61, 175–176.

Nippon Kagaku Zasshi 92, (1971), 1, 80–82.
Tetrahedron Letters 1971, 47, 4503–4506.
Nippon Nogei Kagaku Kaishi 1973, 47, (1), 23–36.
Bl. 1966, 5, 1,763–1,765.
J. of Pharmaceutical Sciences 63, 149, (1974).

*Primary Examiner*—Glennon H. Hollrah
*Assistant Examiner*—James H. Turnipseed
*Attorney, Agent, or Firm*—Finnegan, Henderson, Farabow, Garrett & Dunner

[57] ABSTRACT

Isoquinoline-4-carboxylic acid derivatives of the formula I

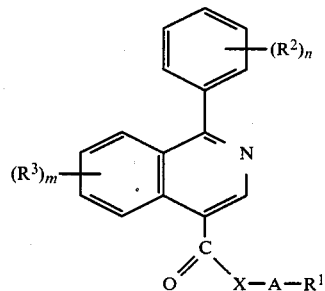

in which m, n, $R^1$, $R^2$, $R^3$, A and X have the meansings indicated, and physiologically acceptable acid addition salts thereof, a process for their preparation, pharmaceutical formulations based on these compounds and the use thereof as antiarrythmic agents.

10 Claims, No Drawings

ISOQUINOLINE DERIVATIVES, PHARMACEUTICAL FORMULATIONS BASED ON THESE COMPOUNDS AND THE USE THEREOF

Isoquinoline derivatives having substituents in the 4-position have been described frequently in the literature, for example Nippon Kagaku Zasshi 92, (1971) 1, 80–82 or Tetrahedron Letters 1971, 47, 4503–4506, but biological effects have not been indicated. 4-(4,5-dihydro-2-imidazolylamino)-isoquinoline derivatives having antihypertensive properties are, inter alia, described in Belgian Pat. No. 875,797, and isoquinoline derivatives possessing an antispasmodic activity similar to that of papaverine are mentioned in Netherlands Patent Application 7,010,358. 4-Amino-6,7-dimethoxyisoquinoline is described as a hypotensive substance in the journal J. of Pharmaceutical Sciences 63, 149 (1974).

It was therefore surprising to find that isoquinoline-4-carboxylic acid derivatives having basic substituents possess an antiarrythmic action.

The present invention therefore relates to isoquinoline-4-carboxylic acid derivatives of the formula I

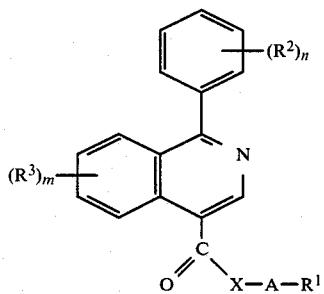

and physiologically acceptable salts thereof, to a process for the preparation of these compounds, to their use as medicaments and to pharmaceutical formulations containing these compounds.

In the formula I:

m and n denote one or two,

X denotes oxygen or nitrogen which is substituted by hydrogen or $C_1$–$C_6$-alkyl, A denotes a bond or a linear or branched $C_1$–$C_8$-alkylene chain, $R^1$ either denotes an amino group of the formula

in which $R^4$ and $R^5$ are identical or different and denote hydrogen or linear or branched $C_1$–$C_8$-alkyl radicals, or $R^1$ denotes a 3-membered to 8-membered ring which contains a nitrogen atom and in which the nitrogen atom is optionally substituted by hydrogen or $C_1$–$C_8$-alkyl and in which one —$CH_2$— group can be replaced by oxygen, sulfur or the —NH— or —N—$C_1$–$C_8$-alkyl group, subject to the proviso that the hetero-atoms in the side chain (—X—A—$R^1$) are separated by at least 2 carbon atoms, $R^2$ denotes hydrogen, halogen, hydroxyl, nitro, amino or $C_1$–$C_6$-alkyl or $C_1$–$C_6$-alkoxy radicals and $R^3$ denotes hydrogen, halogen, hydroxyl, nitro, amino, $C_1$–$C_6$-alkyl or $C_1$–$C_6$-alkoxy radicals or a benzyloxy, methylenedioxy or ethylenedioxy group.

In particular, the invention embraces compounds in which m and n denote one or two, X denotes oxygen or nitrogen which is substituted by hydrogen or $C_1$–$C_4$-alkyl, A denotes a bond or a linear or branched $C_1$–$C_6$-alkylene chain, $R^1$ either denotes an amino group of the formula

in which $R^4$ and $R^5$ are identical or different and denote hydrogen or linear or branched $C_1$–$C_6$-alkyl radicals, or $R^1$ denotes a 3-membered to 6-membered ring which contains a nitrogen atom and in which the nitrogen atom is optionally substituted by hydrogen or $C_1$–$C_6$-alkyl and in which a —$CH_2$— group can be replaced by oxygen, sulfur or the —NH— or —N—$C_1$–$C_6$-alkyl group, subject to the proviso that the hetero-atoms in the side chain are separated by at least 2 carbon atoms, $R^2$ denotes hydrogen, halogen, hydroxyl, nitro, amino or $C_1$–$C_4$-alkyl or $C_1$–$C_4$-alkoxy radicals and $R^3$ represents hydrogen, halogen, hydroxyl, nitro, amino or $C_1$–$C_4$-alkyl or $C_1$–$C_4$-alkoxy radicals.

Particularly preferred compounds are those in which m and n denote one or two, X denotes oxygen or nitrogen which is substituted by hydrogen or a methyl or ethyl radical, A denotes a bond or a linear or branched $C_1$–$C_4$-alkylene chain, in particular the methylene, ethylene, propylene, iso-propylene, butylene and iso-butylene chain, $R^1$ either denotes an amino group of the formula

in which $R^4$ and $R^5$ are identical or different and denote hydrogen or linear or branched $C_1$–$C_4$-alkyl radicals, in particular the methyl, ethyl, propyl and butyl radical, or $R^1$ denotes a 3-membered to 6-membered ring which contains a nitrogen atom, in particular the aziridino, pyrrolidino and piperidino ring, in which the nitrogen optionally carries hydrogen, methyl, ethyl, propyl, iso-propyl or butyl, or the piperazino ring, which can be substituted by the said alkyl radicals, subject to the proviso that the hetero-atoms in the side chain are separated by at least 2 carbon atoms, $R^2$ denotes hydrogen, fluorine, chlorine, bromine, hydroxyl, amino, methyl, ethyl, methoxy or ethoxy, preferably in the ortho-position and/or para-position, and $R^3$ represents hydrogen, fluorine, chlorine, bromine, hydroxyl, amino, methyl, ethyl, methoxy or ethoxy, preferably in the 6-position and/or 7-position.

Compounds which are of very particular interest are those in which n denotes one, X denotes oxygen or nitrogen which carries hydrogen, A denotes a linear $C_2$–$C_3$-alkylene group, $R^1$ denotes an amino group of the formula

in which $R^4$ and $R^5$ are identical and represent $C_1$-$C_3$-alkyl, $R^2$ denotes hydrogen or $C_1$-$C_3$-alkyl and $R^3$ denotes hydrogen.

The process for the preparation of the compounds of the formula I comprises reacting compounds of the formula II

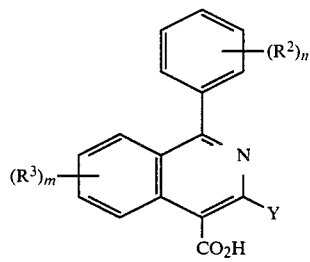
(II)

wherein m, n, $R^2$ and $R^3$ have the meaning mentioned for formula I and Y denotes hydrogen or halogen, with an amine or alcohol of the formula HX—A—$R^1$ in which X, A and $R^1$ have the abovementioned meaning, dehalogenating the resulting compound in which Y denotes halogen and, if desired, converting the reaction products into their physiologically acceptable acid addition salts.

The reaction of the carboxylic acids of the formula II with an amine or alcohol of the formula HX—A—$R^1$ is effected in accordance with methods known per se, advantageously in the presence of a condensation agent, such as, for example, thionyl chloride. The substituent Y is preferably hydrogen or chlorine.

The compounds II are either described in the literature or can be prepared analogously to the methods described in the literature, the following methods are particularly suitable:

(a) Nippon Nogei Kagaku Kaishi 1973, 47, (1), 23–36

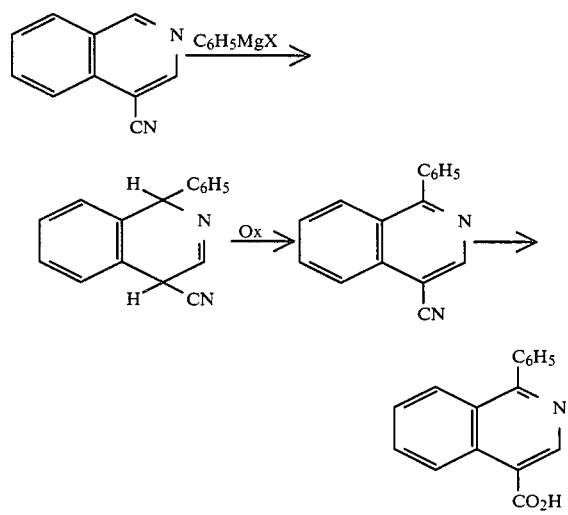

(b) Bl. 1966, 5, 1,763–1,765:

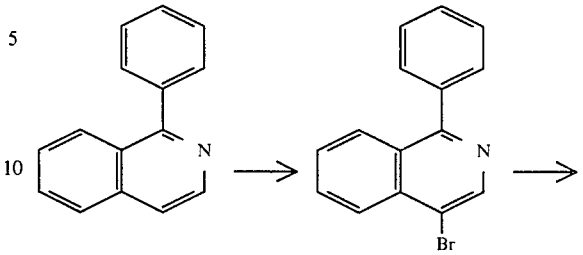

(c) Another method of preparing the compounds II starts from 3-chloro-1-phenylisoquinoline-4-carboxylic acids, which are described in German Offenlegungsschrift 2,818,423:

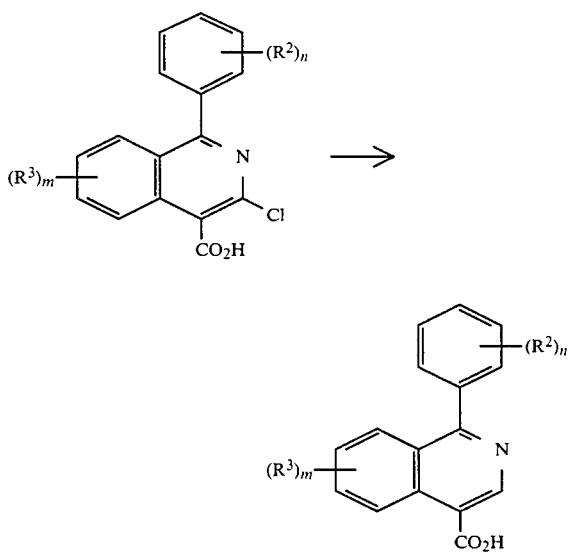

The dehalogenation is best carried out by catalytic hydrogenation, for example using palladium on animal charcoal or platinum oxide in methanol, or other solvents which are customary for hydrogenation, at temperatures between 20° and 100° C. and under a hydrogen pressure of 1–100 atmospheres, in the presence of a base, such as, for example, ammonia or sodium hydroxide.

If the two reaction stages dehalogenation and amide formation are exchanged, using as starting material, for example, 3-chloro-1-phenylisoquinoline-4-carboxylic acids, the following sequence of synthesis results for the preparation of the compound I:

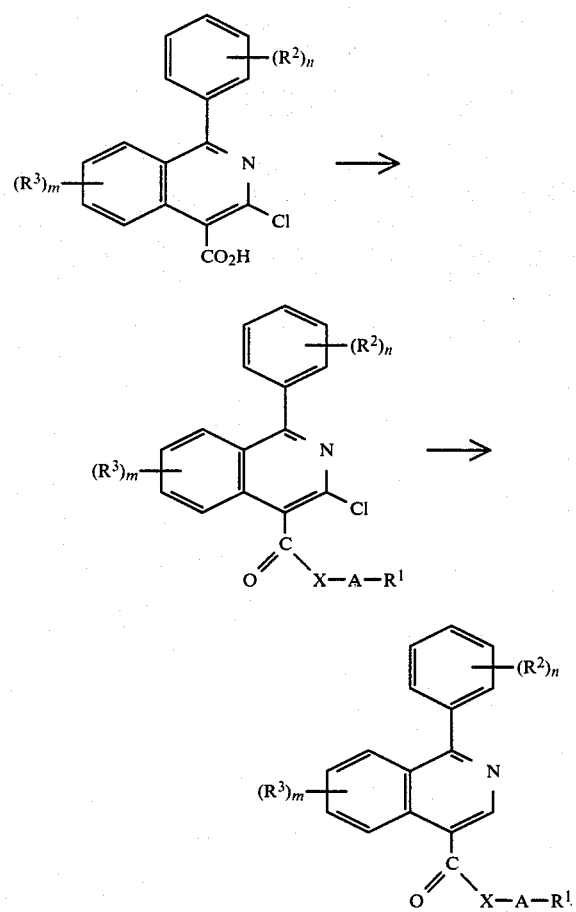

The dehalogenation is advantageously carried out as indicated above.

The following compounds can be prepared by these processes: N-(2-(diethylamino)-ethyl)-1-(2,4-dimethylphenyl)-isoquinoline-4-carboxylic acid amide, 2-(diethylamino)-ethyl 1-(2,4-dimethylphenyl)-isoquinoline-4-carboxylate, N-(2-(diethylamino)-ethyl)-1-(2,3-dimethylphenyl)-isoquinoline-4-carboxylic acid amide, N-(2-diethylamino)-ethyl)-6-methoxy-1-(2-methylphenyl)-isoquinoline-4-carboxylic acid amide, N-(2-diethylamino)-ethyl)-6-hydroxy-1-(2-methylphenyl)-isoquinoline-4-carboxylic acid amide, N-(2-(diethylamino)-ethyl)-6-methyl-1-(2-methylphenyl)-isoquinoline-4-carboxylic acid amide, 3-(diethylamino)-propyl 1-(2-methylphenyl)-isoquinoline-4-carboxylate, N-(2-(diethylamino)-ethyl)-1-(4-methoxyphenyl)-isoquinoline-4-carboxylic acid amide, 1-(2-chlorophenyl)-N-(3-dimethylamino)-propyl)-isoquinoline-4-carboxylic acid amide, 2-(piperidin-1-yl)-ethyl 1-phenylisoquinoline-4-carboxylate, 2-(morpholin-4-yl)-ethyl 1-phenylisoquinoline-4-carboxylate, N-(2-(diethylamino)-ethyl)-N-ethyl-1-phenylisoquinoline-4-carboxylic acid amide, N-(2-(diethylamino)-ethyl)-N-ethyl-1-(4-methylphenyl)-isoquinoline-4-carboxylic acid amide, N-(2-(diethylamino)-ethyl)-1-(2-methoxyphenyl)-isoquinoline-4-carboxylic acid amide, 3-(diethylamino)-propyl 1-(2-hydroxyphenyl)-isoquinoline-4-carboxylate, N-(2-(diethylamino)-ethyl)-6,7-dimethoxy-1-(2,4-dimethylphenyl)-isoquinoline-4-carboxylic acid amide, 3-(dimethylamino)-propyl 6,7-dimethyl-1-phenylisoquinoline-carboxylate, N-(2-(diethylamino)-ethyl)-6,8-dimethyl-1-(2-methylphenyl)-isoquinoline-4-carboxylic acid amide, N-(3-(dimethylamino)-2-propyl)-1-(2-methylphenyl)-isoquinoline-4-carboxylic acid amide, N-(2-(dimethylamino)-3-propyl)-1-(2-methylphenyl)-isoquinoline-4-carboxylic acid amide, 1-(2-chlorophenyl)-N-(3-(dimethylamino)-2-propyl)-isoquinoline-4-carboxylic acid amide, 6-chloro-N-(2-(diethylamino)-ethyl)-1-(2-methylphenyl)-isoquinoline-4-carboxylic acid amide, 3-(dimethylamino)-propyl 7-methoxy-1-phenylisoquinoline-4-carboxylate, N-(2-(diisopropylamino)-ethyl)-1-(2-methylphenyl)-isoquinoline-4-carboxylic acid amide, 1-(4-aminophenyl)-N-(2-(diethylamino)-ethyl)-isoquinoline-4-carboxylic acid amide, N-(3-(diethylamino)-propyl)-1-(4-hydroxyphenyl)isoquinoline-4-carboxylic acid amide, N-(2-(dibutylamino)-ethyl-1-phenylisoquinoline-4-carboxylic acid amide, N-(2-(ethylamino)-ethyl)-1-phenylisoquinoline-4-carboxylic acid amide, 3-(ethylamino)-propyl 1-phenylisoquinoline-4-carboxylate, N-(3-(ethylamino)-2-propyl)-1-(2-methylphenyl)-isoquinoline-4-carboxylic acid amide, N-(2-diethylamino)-ethyl)-7-methyl-1-(2-methylphenyl)-isoquinoline-4-carboxylic acid amide, N-(2-(diisopropylamino)-ethyl)-1-(2,3-dimethylphenyl)-isoquinoline-4-carboxylic acid amide, 3-(diethylamino)-propyl 7-fluoro-1-phenylisoquinoline-carboxylate, N-(3-(diethylamino)-2-propyl)-6,7-dimethoxy-1-(2-methylphenyl)-isoquinoline-4-carboxylic acid amide, 1-(4-chlorophenyl)-N-(2-(diisopropylamino)-ethyl-isoquinoline-4-carboxylic acid amide, 1-(4-amino-2-methylphenyl)-N-(2-(diethylamino)-ethyl)-isoquinoline-4-carboxylic acid amide, N-(4-(diethylamino)-2-butyl)-1-(2-methylphenyl)-isoquinoline-4-carboxylic acid amide, 1-(4-hydroxyphenyl)-N-(2-(thiomorpholin-4-yl)-ethyl-)isoquinoline-4-carboxylic acid amide, N-(2-(dipropylamino)-ethyl)-1-(2-methylphenyl)-isoquinoline-4-carboxylic acid amide, 2-(dibutylamino)-ethyl 1-(2,3-dimethylphenyl)-isoquinoline-4-carboxylate, N-(2-(diethylamino)-ethyl)-1-(3-nitrophenyl)-isoquinoline-4-carboxylic acid amide, N-(2-(diethylamino)-ethyl)-7-nitro-1-phenylisoquinoline-4-carboxylic acid amide, 1-(2-methylphenyl)-N-(2-(pyrrolidin-1-yl)-ethyl)-isoquinoline-4-carboxylic acid amide, 1-(2,3-dimethylphenyl)-N-(2-(4-methylpiperazin-1-yl)-ethyl)-isoquinolin-4-carboxylic acid amide, 1-methylpiperidine-3-yl 1-phenylisoquinoline-4-carboxylate, N-((1-ethylpyrrolidin-2-yl)-methyl)-1-(4-methoxyphenyl)-isoquinoline-4-carboxylic acid amide, piperidin-4-yl 1-(2-methylphenyl)-isoquinoline-4-carboxylate, (1-methylpyrrolidin-3-yl)-methyl 1-(2-chlorophenyl)-isoquinoline-4-carboxylate, N-((1-methylpyrrolidin-3-yl)-methyl)-1-(2-fluorophenyl)-isoquinoline-4-carboxylic acid amide, N-(1-methylpiperidin-4-yl)-1-phenylisoquinoline-4-carboxylic acid amide, N-((1-ethylpiperidin-2-yl)-methyl)-1-(4-hydroxyphenyl)-isoquinoline-4-carboxylic acid amide, 6,7-dimethyl-N-((1-ethylpyrrolidin-2-yl)-methyl)-1-(2-methylphenyl)-isoquinoline-4-carboxylic acid amide, 6,7-dimethyl-N-(1-ethylpiperidin-3-yl)-1-phenylisoquinoline-4-carboxylic acid amide, 7-chloro-N-(1-methylpiperidin-3-yl)-1-(2-methylphenyl)-isoquinoline-4-carboxylic acid amide, 6-fluoro-N-(piperidin-3-yl)-1-phenylisoquinoline-4-carboxylic acid amide, (1-ethylpyrrolidin-2-yl)-methyl 6,7-dimethyl-1-phenylisoquinoline-4-carboxylate, N-((1-isopropylpyrrolidin-2-yl)-methyl)-1-(2-methylphenyl)-isoquinoline-4-carboxylic acid amide, 3-diethylamino-2-propyl 6-methoxy-1-(4-nitrophenyl)-isoquinoline-4-carboxylate, 2-(diethylamino)-ethyl 1-(2-chloro-6-fluorophenyl)-isoquinoline-4-carboxylate, N-(2-diethylamino)-ethyl)-1-(2-chloro-6-fluorophenyl)-isoquinoline-4-carboxylic acid amide, 1-ethylpiperidin-4-yl 1-(2-chlorophenyl)-isoquinoline-4-carboxylate, N-((2-isopropylamino)-ethyl)-6-methyl-1-(2-methylphenyl)-isoquinoline-4-carboxylic acid amide, N-((1-methylpyrrolidin-3-yl)-methyl)-1-(2,3-dimethylphenyl)-isoquinoline-4-carboxylic acid amide, N-(1-isopropylpiperidin-4-yl)-1-(2-chlorophenyl)-isoquinoline-4-carboxylic acid amide, 1-(4-aminophenyl)-N-((1-methylpiperidin-2-yl)-methyl)-isoquinoline-4-carboxylic acid amide, N-(2-(diethylamino)-ethyl)-1-(4-hydroxyphenyl)-6-methyl-isoquinoline-4-carboxylic acid amide and N-((1-ethyl-pyrrolidin-2-yl)-methyl)-1-(4-hydroxyphenyl)-6-methoxyisoquinoline-4-carboxylic acid amide.

The compounds according to the invention are new compounds and have valuable therapeutic properties. Thus, for example, they exhibit an action on the cardiovascular system. In particular, they abolish arrythmia caused in dogs by strophanthin. By virtue of this property the compounds according to the invention can be used as active compounds in medicaments having an antiarrythmic action.

The pharmacological tests were carried out as follows: 35 mg/kg of Nembutal are administered intraperitoneally to produce an anesthesia in a dog of either sex. The blood pressure is measured via pressure transducers from the carotid artery and is recorded in a customary manner. The ECG is recorded at the extremities by means of puncture electrodes. The electrode showing the least disturbance (in most cases electrode II) is displayed on an oscilloscope and is also recorded via a direct recorder. The heart rate is determined electronically from the R-waves of the ECG and is also displayed continuously as a curve on the direct recorder. Strophanthin k is now administered to the dog as an intravenous drip via a vein in the leg (4 mcg/kg/ml and minute) until ventricular extrasystoles appear. If the disturbances persist over a period of about 5 minutes without the administration of further strophanthin, the drip is terminated. A test is now made to determine whether the test substance is capable of removing the disturbances. Only an immediate disappearance of the extrasystoles in the case of intravenous administration or disappearance within 15 minutes in the case of i.d. administration is rated successful. The substance is administered as a 5% strength solution in doses of 1 and 3 mg/kg. A formulation which, in the doses indicated, causes at least a clear reduction in the number of extrasystoles is designated effective. A strong action exists if a formulation completely eliminates the ventricular extrasystoles for a period of about 20 minutes when administered intravenously.

The results are listed in Table I.

TABLE I

| Compound according to Example No. | Structural formula | Antiarrythmic effect on dogs poisoned with strophanthin (intravenously) | |
|---|---|---|---|
| | | Strength of action | Duration of action |
| 1 | (isoquinoline with 2-methylphenyl at C1 and CONHCH₂CH₂N(C₂H₅)₂ at C4) | very strong | very long |
| 2 | (isoquinoline with 2-methylphenyl at C1 and CO₂CH₂CH₂N(CH₃)₂ at C4) | strong | very long |
| 3 | (isoquinoline with phenyl at C1 and CONHCH₂CH₂CH₂N(CH₃)₂ at C4) | strong | long |

The compounds according to the invention and their pharmacologically acceptable salts are effective as antiarrythmic agents within a wide range of dosage. Thus 50–100 mg per day can be injected intravenously into an adult or 100–300 mg per day can be administered perorally to an adult.

The new compounds can be used either on their own or with physiologically acceptable auxiliaries or excipients. For an oral application form, the active compounds are mixed with the substances customary for this purpose and are converted by customary methods into suitable forms for administration, such as tablets, capsules, aqueous, alcoholic or oily suspensions or aqueous, alcoholic or oily solutions. Examples of inert excipients which can be used are magnesium carbonate, lactose or corn starch. Formulation can be effected in the form of either dry or moist granules. Examples of suitable oily excipients or solvents are, in particular, vegetable and animal oils, such as, for example, sunflower oil or fish-liver oil.

Intravenous administration constitutes a special form of administration. For this purpose, the active compounds or physiologically acceptable salts thereof are dissolved by means of the substances which are customary for this use. Physiologically acceptable salts of this type are formed, for example, with the following acids: hydrochloric, hydrobromic or hydriodic acid, phosphoric acid, sulfuric acid, methylsulfuric acid, sulfamic acid, nitric acid, formic acid, acetic acid, propionic acid, succinic acid, tartaric acid, lactic acid, malonic acid, fumaric acid, oxalic acid, citric acid, malic acid, mucic acid, benzoic acid, salicylic acid, acetylaminoacetic acid, 4,4'-methylene-bis-(3-hydroxy-2-naphthoic acid) (embonic acid), naphthalene-1,5-disulfonic acid, ascorbic acid, phenylacetic acid, p-aminosalicylic acid, hydroxyethanesulfonic acid, benzenesulfonic acid or synthetic resins containing acid groups, for example resins having an ion exchange action. Examples of suitable solvents for the appropriate physiologically acceptable salts of the active compounds for intravenous administration are: water, physiological sodium chloride solutions or an alcohol, such as, for example, ethanol, propanediol or glycerol, and also sugar solutions, such as, for example, solutions of glucose or mannitol, or a mixture of the various solvents mentioned.

EXAMPLE 1

N-(2-(Diethylamino)-ethyl)-1-(2-methylphenyl)-isoquinoline-4-carboxylic acid amide 6.6 g of 1-(2-methylphenyl)-isoquinoline-4-carboxylic acid in 100 ml of thionyl chloride are heated for 5 hours at 50° C. The excess thionyl chloride is removed in vacuo and the residue is taken up in toluene and again concentrated in vacuo. The acid chloride thus obtained is dissolved in 50 ml of chloroform and the solution is added dropwise at 0°–10° C. to 8.67 g of 2-diethylaminoethylamine in 140 ml of chloroform. The reaction mixture is allowed to stand overnight at room temperature, the chloroform is removed in vacuo and the residue is partitioned between toluene and saturated sodium bicarbonate solution. The toluene phase is dried with magnesium sulfate and concentrated. The light brown oil is dissolved in a little ethanol, and an equimolar quantity of hydrogen chloride in ethanol is added. After concentrating the mixture and dissolving the residue in acetone 5.1 g crystallize out in the form of the hydrochloride in pale yellow crystals of melting point 175°–177° C.

The starting material, 1-(2-methylphenyl)-isoquinoline-4-carboxylic acid can be prepared by catalytic dehalogenation from 3-chloro-1-(2-methylphenyl)-isoquinoline-4-carboxylic acid:

40 g of 3-chloro-1-(2-methylphenyl)-isoquinoline-4-carboxylic acid are dissolved in 800 ml of methanol and 200 ml of methanolic ammonia, 2 g of 10% strength palladium on animal charcoal are added and the mixture is hydrogenated for 6 hours at 70° C. and 50 atmospheres pressure of hydrogen. The solution is filtered and concentrated and the residue is taken up in water. The pH is adjusted to 2 with 2N hydrochloric acid and the precipitated acid is filtered off. Melting point 254° C.

EXAMPLE 2

(2-Dimethylamino)-ethyl 1-(2-methylphenyl)-isoquinoline-4-carboxylate 6.6 g of 1-(2-methylphenyl)-isoquinoline-4-carboxylic acid are converted into the acid chloride using 100 ml of thionyl chloride at 50° C. for 5 hours. After removing the excess thionyl chloride, the acid chloride is dissolved in 50 ml of chloroform and the solution is added dropwise at 0°–10° C. to 6.69 g of 2-dimethylaminoethanol in 140 ml of chloroform. After 10 hours at room temperature the chloroform is removed, and the residue is partitioned in toluene and saturated sodium bicarbonate solution. 6.0 g of a brown oil are isolated from the toluene phase; this oil in ethanolic hydrochloric acid gives 3.7 g of the hydrochloride of the desired compound, melting point 176°–179° C.

The following compounds of the formula I were prepared analogously to Example 1: (Table II)

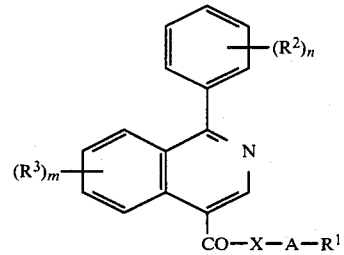

TABLE II

| Example No. | —X—A—R$^1$ | (R$^2$)$_n$ | (R$^3$)$_m$ | Salt/melting point °C. |
|---|---|---|---|---|
| 3 | NH—(CH$_2$)$_3$N(CH$_3$)$_2$ | H | H | Oxalate/125–126 |
| 4 | NH(CH$_2$)$_2$—N(C$_2$H$_5$)$_2$ | H | 6.7-di-CH$_3$O | Dihydrochloride/162–164 |
| 5 | NH—(CH$_2$)$_3$N(CH$_3$)$_2$ | 2-CH$_3$ | H | Hydrochloride/205–207 |
| 6 | NH—(CH$_2$)$_2$N(C$_2$H$_5$)$_2$ | 2-CH$_3$ | 6.7-di-CH$_3$O | Hydrochloride/100–102 |
| 7 | NH—(CH$_2$)$_3$—N—(CH$_3$)$_2$ | 2-CH$_3$ | 6.7-di-CH$_3$O | Hydrochloride/amorphous |
| 8 | NH—(CH$_2$)$_3$N(CH$_3$)$_2$ | H | 6.7-di-CH$_3$O | Dihydrochloride/203–205 |
| 9 | NH—(CH$_2$)$_2$N(C$_2$H$_5$)$_2$ | H | 6-CH$_3$ | Hydrochloride/206–207 |
| 10 | NH(CH$_2$)$_2$N(C$_2$H$_5$)$_2$ | 4-CH$_3$ | H | Hydrochloride/176–178 |
| 11 | NH(CH$_2$)$_2$N(C$_2$H$_5$)$_2$ | 3-NH$_2$ | H | Hydrochloride/amorphous |

TABLE II-continued

| Example No. | —X—A—R¹ | $(R^2)_n$ | $(R^3)_m$ | Salt/melting point °C. |
|---|---|---|---|---|
| 12 | N—(CH₂)₂N(C₂H₅)₂<br>\|<br>C₂H₅ | 2-CH₃ | H | Hydrochloride/amorphous |
| 13 | CH₃<br>\|<br>O—CH—CH₂—N(C₂H₅)₂ | 2-CH₃ | H | Hydrochloride/166–168 |
| 14 | O—CH₂CH₂—N(CH(CH₃)₂)₂ | 2-CH₃ | H | Hydrochloride/199–201 |
| 15 | O—⟨cyclohexyl⟩—N—CH₃ | 2-CH₃ | H | Oxalate/170–173 |
| 16 | NH(CH₂)₃N(C₃H₇)₂ | 2-CH₃ | H | Hydrochloride/200–201 |
| 17 | NH(CH₂)₄N(C₂H₅)₂ | 2-CH₃ | H | Hydrochloride/168–170 |

EXAMPLE 18:

N-(2-(Diethylamino)-ethyl)-1-phenylisoquinoline-4-carboxylic acid amide 5.2 g of 3-chloro-N-(2-(diethylamino)-ethyl)-1-phenylisoquinoline-4-carboxylic acid amide are suspended in 225 ml of methanol and 30 ml of methanolic ammonia, 1 g of 10% strength palladium on animal charcoal is added and the mixture is hydrogenated at 40° C. and 1 atmosphere of hydrogen. When the calculated quantity of hydrogen has been taken up, the catalyst is filtered off and the filtrate is concentrated and partitioned between toluene and aqueous potassium carbonate solution. The toluene phase is washed with water, dried, filtered and concentrated. The residual 3.8 g of a pale yellow oil are dissolved in isopropanol, and precipitated as the oxalate by means of the equivalent quantity of oxalic acid is isopropanol. This gives 4.6 g of oxalate, melting point 115–118, with decomposition.

The starting material 3-chloro-N-(2-(diethylamino)-ethyl)-1-phenylisoquinoline-4-carboxylic acid amide is prepared by the following route.

42.5 g of 3-chloro-1-phenylisoquinoline-4-carboxylic acid in 300 ml of thionyl chloride are heated on a steam bath for 4 hours. The excess thionyl chloride is removed in vacuo, toluene is added to the residue and the mixture is again concentrated in vacuo. 11.3 g of the resulting acid chloride in 75 ml of chloroform are added dropwise, at 20° C., to 13.1 g of diethylaminoethylamine in 100 ml of chloroform. After standing for 20 hours at room temperature, the mixture is partitioned between toluene and water. 14 g of a brown oil are isolated from the toluene phase; this oil in ethanolic oxalic acid gives a crystalline oxalate of melting point 167°–169° C.

EXAMPLE 19

N-(2-(Diethylamino)-ethyl)-1-phenylisoquinoline-4-carboxylic acid amide 5.2 g of 1-phenylisoquinoline-4-carboxylic acid are converted into the acid chloride by means of 100 ml of thionyl chloride. The crude acid chloride is dissolved in 20 ml of chloroform and the solution is added dropwise, at 0°–10° C., to 8.6 g of diethyalminoethylamine in 100 ml of chloroform. The reaction solution is stirred for 10 hours at room temperature, the solvent is removed in vacuo and the residue is partitioned between toluene and water. 4.1 g of a pale yellow oil are isolated from the toluene solution; with the equimolar quantity of oxalic acid in isopropanol, this oil gives the crystalline oxalate, melting point 115°–118°, with decomposition.

The starting material, 1-phenylisoquinoline-4-carboxylic acid is prepared by the following route.

20.5 g of 1-phenylisoquinoline are dissolved in 100 ml of carbon tetrachloride, and 16 g of bromine are added at room temperature. The temperature is raised slowly and the mixture is kept under reflux for 1 hour. 7.9 g of pyridine in 10 ml of carbon tetrachloride are added dropwise to the boiling reaction mixture in the course of 2 hours, and the mixture is then heated at reflux temperature for a further 18 hours. The reaction solution is decanted off from the resinous precipitate and is concentrated, and the residue is crystallized from diisopropyl ether. 11.7 g of 4-bromo-1-phenylisoquinoline of melting point 123°–125° C. are obtained. 0.7 g of 4-bromo-1-phenylisoquinoline, 0.45 g of copper cyanide and 10 ml of dimethylformamide are heated at 160° C. for 6 hours. The reaction solution is decanted off, diluted with methylene chloride and washed with water. 0.75 g of crude product are isolated from the methylene chloride phase, and 0.2 g of 4-cyano-1-phenylisoquinoline of melting point 138°–140° is obtained from this crude product by column chromatography over silica gel using a 98:2 mixture of chloroform and ethyl acetate. 0.2 g of 4-cyano-1-phenylisoquinoline is heated with 10 ml of 20% strength sodium hydroxide solution at 100° C. for 4 hours. The solution is cooled and acidified with acetic acid. The precipitate is filtered off and dried. 0.18 g of 1-phenylisoquinoline-4-carboxylic acid of melting point 215°–217° is isolated.

We claim:

1. An isoquinoline-4-carboxylic acid derivative of the formula I

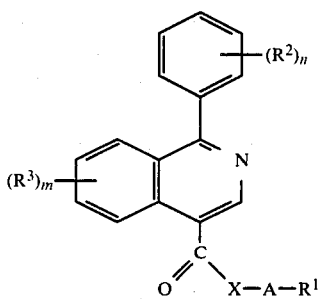

in which m and n denote one or two,

X denotes oxygen or nitrogen which is substituted by hydrogen or $C_1$–$C_6$-alkyl, A denotes a bond or a linear or branched $C_1$–$C_8$-alkylene chain, $R^1$ either denotes an amino group of the formula

in which $R^4$ and $R^5$ are identical or different and denote hydrogen or linear or branched $C_1$–$C_8$-alkyl radicals, or $R^1$ denotes a 3-membered to 6-membered ring which has a nitrogen atom in the ring and in which the nitrogen atom is unsubstituted or substituted by hydrogen or $C_1$–$C_8$-alkyl and in which one —$CH_2$— group can be replaced by oxygen, sulfur or the —NH— or —N—$C_1$–$C_8$-alkyl group, subject to the proviso that the hetero-atoms in the side chain (—X—A—$R^1$) are separated by at least 2 carbon atoms, $R^2$ denotes hydrogen, fluorine, chlorine, bromine, hydroxyl, nitro, amino, $C_1$–$C_6$-alkyl or $C_1$–$C_6$-alkoxy radicals, and $R^3$ denotes hydrogen, fluorine, chlorine, bromine, hydroxyl, nitro, amino, $C_1$–$C_6$-alkyl or $C_1$–$C_6$-alkoxy radicals or a benzyloxy, methylenedioxy or ethylenedioxy group, or a physiologically acceptable acid addition salt thereof.

2. An isoquinoline-4-carboxylic acid derivative of the formula I indicated in claim 1, in which n is one, X is oxygen or nitrogen which is substituted by hydrogen, A is a linear $C_2$ to $C_3$ alkylene group, $R^1$ is an amino group of the formula

in which $R^4$ and $R^5$ are identical and represent $C_1$–$C_3$-alkyl radicals, $R^2$ is hydrogen or $C_1$–$C_3$-alkyl and $R^3$ is hydrogen, or a physiologically acceptable acid addition salt thereof.

3. The compound N-(2-diethylamino)-ethyl)-1-(2-methylphenyl)-isoquinoline-4-carboxylyic acid amide or its hydrochloric acid salt.

4. A pharmaceutical formulation containing a pharmaceutically effective amount of a compound as claimed in claim 1.

5. A method of treating a host having arrythmias which comprises administering to said host a pharmaceutically effective dosage of a compound as claimed in claim 1.

6. The method as claimed in claim 5 wherein from 50 to 100 mg per day of said compound is injected intravenously into said host.

7. The method as claimed in claim 5 wherein from 100 to 300 mg per day of said compound is administered perorally to said host.

8. A method of treating a host having arrythmias which comprises administering to said host a pharmaceutically effective dosage of a compound as claimed in claim 3.

9. The method as claimed in claim 8 wherein from 50 to 100 mg per day of said compound is injected intravenously into said host.

10. The method as claimed in claim 8 wherein from 100 to 300 mg per day of said compound is administered perorally to said host.

* * * * *